United States Patent [19]

Kawabata

[11] Patent Number: 4,950,774
[45] Date of Patent: Aug. 21, 1990

[54] 2-5,DISUBSTITUTED-7,7,8,8-TETRACYANOQUINODIMETHANES

[75] Inventor: Takeo Kawabata, Hirakata, Japan

[73] Assignee: Nippon Gohsei Kagaku Kogyo Kabushiki, Osaka, Japan

[21] Appl. No.: 111,744

[22] Filed: Oct. 23, 1987

[30] Foreign Application Priority Data

Oct. 27, 1986 [JP] Japan .................. 61-256255

[51] Int. Cl.$^5$ .......................... C07C 255/31
[52] U.S. Cl. ...................... 552/303; 252/500; 558/430; 560/126; 562/508; 564/152
[58] Field of Search ............ 260/396 N; 552/303

[56] References Cited

U.S. PATENT DOCUMENTS 3,115,506 12/1963 Acker et al. .............. 260/396 N
4,772,432 9/1988 Miyashita ................ 260/396 N

FOREIGN PATENT DOCUMENTS 26260 2/1987 Japan ..................... 260/396 N

OTHER PUBLICATIONS

J. Am. Chem. Soc., 84, 3370 (1962)–"Substituted Quinodimethans, I, Preparation and Chemistry of 7,7,8,8-Tetracyanoquinodimethan".
J. Am. Chem. Soc. 84, 3374 (1962)–"Substituted Quinodimethans, II, Anion-Radical Derivatives and Complexes of 7,7,8,8-Tetracyanoquinodimethan."

Primary Examiner—Vivian Garner
Attorney, Agent, or Firm—Armstrong, Nikaido, Marmelstein, Kubovcik & Murray

[57] ABSTRACT

A 2,5-disubstituted-7,7,8,8-tetracyanoquinodimethane of the general formula

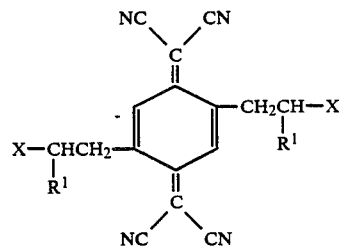

wherein $R^1$ is hydrogen or methyl, X is $COOR^2$ (in which $R^2$ is hydrogen or $C_{1-10}$ alkyl), $-CONR^3R^4$ (in which $R^3$ and $R^4$ each is hydrogen or $C_{1-4}$ alkyl) or $-CN$, provided that when $R^1$ is hydrogen, X is $-CN$ or $-CONR^3R^4$. The tetracyanoquinodimethane derivatives are starting materials for the production of polyamides, polyurethanes or organic semiconductor devices.

4 Claims, No Drawings

2-5,DISUBSTITUTED-7,7,8,8-TETRACYANOQUINODIMETHANES

BACKGROUND OF THE INVENTION

This invention relates to novel tetracyanoquinodimethane derivatives which are of value as starting materials for the production of polyesters, polyamides, polyurethanes, etc. or for the manufacture of organic semiconductor devices.

7,7,8,8-Tetracyanoquinodimethane (TCNQ) occurs as yellow crystals melting at 293.5 to 296° C. This compound is ready to accept one electron to form a stable anion radical and its derivatives show very small electrical resistance values. Said compound is converted to phenylenedimalononitrile on reduction with thiophenol, mercaptoacetic acid, hydrogen iodide or the like, and the latter is reconverted to TCNQ on oxidation with N-bromosuccinimide. Chemical condensers are among the commercial applications of TCNQ.

A typical process known for the synthesis of TCNQ comprises condensing malononitrile with 1,4-cyclohexanedione and oxidizing the resulting 1,4-bis(dicyanomethylene)cyclohexane with N-bromosuccinimide or bromine in pyridine.

Since TCNQ is thus electrically conductive despite its being an organic compound, it is rewarding to develop processes for synthesizing said compound via other routes or discover conductive compounds skeletally analogous to TCNQ for the research and development of organic conductive substances and for their commercial implementation.

The object of this invention is to provide novel tetracyanoquinodimethane derivatives which are of value as starting materials for the production of polyesters, polyamides, polyurethanes, etc. or for the manufacture of organic semiconductor devices.

The another object of this invention is to provide a process for production of the above-mentioned tetracyanoquinodimethane derivatives.

SUMMARY OF THE INVENTION

The compounds according to the invention are 2,5-disubstituted-7,7,8,8-tetracyanoquinodimethanes having the general formula given below and are novel compounds which have not been described in the literature to this day.

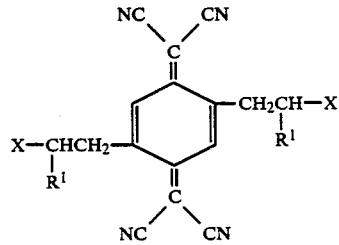
(V)

wherein $R^1$ is hydrogen or methyl; X is $—COOR^2$ (in which $R^2$ is hydrogen or $C_{1-10}$ alkyl), $—CONR^3R^4$ (in which $R^3$ and $R^4$ each is hydrogen or $C_{1-4}$ alkyl) or $—CN$; provided that when $R^1$ is hydrogen, X is $—CN$ or $—CONR^3R^4$.

As the alkyl represented by $R^2$, there may be mentioned those alkyl groups that contain 1 to 10 carbon atoms, such as methyl, ethyl, propyl, butyl, hexyl, octyl, decyl and cyclohexyl, in particular lower alkyl groups containing 1 to 4 carbon atoms. The alkyl group represented by $R^3$ and/or $R^4$ includes lower alkyl groups containing 1-4 carbon atoms, such as methyl, ethyl, propyl and butyl.

Specific examples of the compounds (V) are as follows:

(a) 2,5-Bis(2-cyanoethyl)-7,7,8,8-tetracyanoquinodimethane [in formula (V), $R^1$ is hydrogen and X is CN], (b) 2,5-Bis[2-(alkoxycarbonyl)propyl]-7,7,8,8-tetracyanoquinodimethanes and 2,5-bis(2-carboxypropyl)7,7,8,8-tetracyanoquinodimethane [in formula (V), $R^1$ is methyl and X is $-COOR^2$], (c) 2,5-Bis(2-cyanopropyl)-7,7,8,8-tetracyanoquinodimethane [in formula (V), $R^1$ is methyl and X is $—CN$], and (d) 2,5-Bis[2-dialkylcarbamoyl)ethyl]-7,7,8,8-tetracyanoquinodimethanes [in formula (V), $R^1$ is hydrogen and X is $—CONR^3R^4$].

The compounds of the invention which are represented by the above general formula (V) can be produced by oxidizing a 2,5-disubstituted-cyclohexane1,4-bis(dicyanomethylene) of the general formula

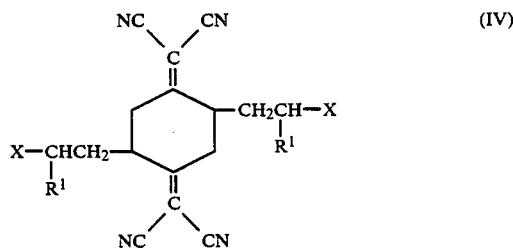
(IV)

wherein $R^1$, X, $R^2$, $R^3$ and $R^4$ are as defined above.

Generally, the oxidation is carried out in an inert gas atmosphere in a solvent, such as acetonitrile, in the presence of a basic substance, such as pyridine, using a halogen (e.g. bromine, chlorine) or an N-halosuccinimide (e.g. N-bromosuccinimide, N-chlorosuccinimide).

This reaction is generally carried out at 70°–80° C. for about 10 minutes to about 1 hour.

The halogen or N-halosuccinimide is used in an amount of 1–5 moles, generally about 2 moles, per mole of the compound (IV).

After completion of the reaction, the product is recovered from the reaction mixture by direct filtration, by filtration following addition of water to precipitate the product, or by filtration following removal of the solvent and addition of water. The product is then purified by conventional purification means, such as washing with water, methanol, acetone, etc., and dried.

The starting materials, namely the compounds (IV), can be prepared by the following route:

First, cyclohexane-1,4-dione (I) is reacted with pyrrolidine (enamination), and the thus-obtained 1,4-dipyrrolidinocyclohexane-1,3-diene (II) is reacted with an unsaturated compound of the general formula

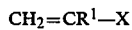

to give a 2,5-disubstituted-cyclohexane-1,4-dione (III) of the general formula:

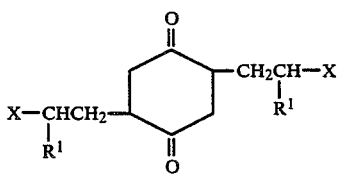

The above reactions can be shown by the following reaction formulas:

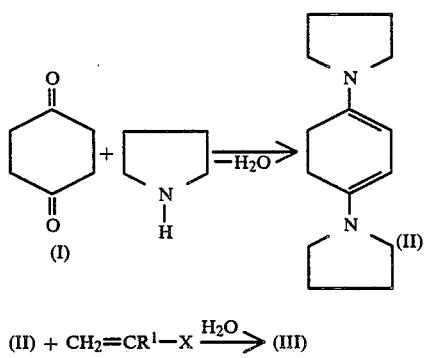

$$(II) + CH_2=CR^1-X \xrightarrow{H_2O} (III)$$

In the first step, the compound (I) is enaminated to give the compound (II).

Benzene, toluene, xylene or the like is used as the solvent for the enamine formation.

The reaction is preferably conducted at a refluxing temperature, while the byproduct water is continuously removed from the reaction system. The use of a catalyst is not always necessary. When required, an acid such as p-toulenesulfonic acid may be used.

It is advantageous to maintain the reaction system in a nitrogen atmosphere so that possible oxidation of the dienamine formed can be prevented, Pyrrolidine is used in an amount selected within the range of 2–4 moles per mole of compound (I).

The reaction period is suitably 1–3 hours.

The solvent and remaining pyrrolidine are removed from the reaction mixture obtained in the first reaction step, and the residue is submitted to the reaction with the above-mentioned unsaturated compound in the second step.

The solvent for the reaction in the second step may be dioxane, dimethylformamide, ethanol, methanol, acetonitrile or the like.

The unsaturated compound is used in an amount of 2–4 moles per mole of compound (I).

The reaction is performed under reflux for about 3–24 hours. Then, about 2 equivalents (relative to cyclohexanedione) of water is added, and refluxing is continued for about 1–2 hours to thereby effect hydrolysis. Thus is obtained the compound (III).

As specific examples of the unsaturated compound, there may be mentioned acrylic acid, alkyl acrylates (methyl acrylate, ethyl acrylate, etc.), methacrylic acid, alkyl methacrylates (methyl methacrylate, ethyl methacrylate, etc.), acrylonitrile, methacrylonitrile, and so on.

The thus-obtained compound (III), namely a 2,5-disubstituted-cyclohexane-1,4-dione is reacted with malononitrile of the formula

NC—CH$_2$—CN to give the compound (IV) according to the following reaction formula:

$$(III) + NC-CH_2-CN \quad (IV)$$

This reaction is generally carried out in a solvent such as water, an alcohol, or a water-alcohol mixture.

In carrying out the reaction, a small amount of a catalyst such as β-alanine, glycine or ammonium acetate is caused to be present in the reaction system.

When X is —COOH, it is advisable to neutralize the compound (III) with an alkaline substance such as sodium hydrogen carbonate in advance as necessary.

Heating (e.g. at 40–60° C.) for about 1–5 hours is sufficient to effect the reaction.

Malononitrile is used generally in an amount of about 2 moles per mole of compound (III). However, malononitrile may be used in excess.

After completion of the reaction, the crystalline precipitate is collected and purified by a conventional method.

For obtaining the compound (IV) in which X is —COOH, two alternative methods are available. According to one, a compound (III) in which X is -COOH is used as the reactant while, according to the other, a compound (III) in which X is —COOR$^2$ (R$^2$ being alkyl) is used and the ester moiety is subsequently hydrolyzed.

For obtaining the compound (IV) in which X is —COOR$^2$ (R$^2$ being alkyl), either a compound (III) in which R$^2$ is alkyl or a compound (III) in which X is —COOH is used as the reactant. When the latter compound is used, the COOH moiety is esterified during the reaction with malononitrile or after said reaction. The simultaneous esterification during the reaction with malononitrile can be effected by conducting said reaction in the presence of an alcohol, whereas the reaction product (IV) in which X is —COOH can be subsequently esterified by converting said reaction product to the acid chloride form by treatment with thionyl chloride or the like and then reacting the acid chloride with an alcohol.

The compounds (V) according to the invention are of value in various applications, for example as starting materials for the production of polyesters, polyamides, polyurethanes, etc., and for the manufacture of organic semiconductor devices.

The series of reactions detailedly described hereinabove may be summarized as follows:

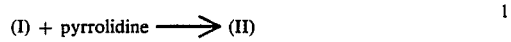      1

      2

      3

      4

The compounds (V) correspond to the compounds provided by the invention, and the reaction corresponds to the process according to the invention.

The compounds (III) themselves are novel compounds and the reaction steps and for obtaining said compounds are also novel processes.

Furthermore, the compounds (IV) are novel compounds as well, and the process for the production of said compounds (IV) is also a novel one.

The invention provides 2,5-disubstituted-7,7,8,8-tetracyanoquinodimethanes which are novel compounds and thereby diversifies the routes to raw materials for the production of polyesters, polyamides, polyurethanes and so forth or for the manufacture of organic semiconductor devices.

EXAMPLES

The following examples are further illustrative of the present invention.

EXAMPLE 1

This example is concerned with 2,5-bis(2-cyanoethyl)7,7,8,8-tetracyanoquinodimethane as an example of the compound (V) of this invention. Hereinafter said compound is referred to as "compound (Va)".

Said compound (Va) is produced by first reacting 2,5-bis(2-cyanoethyl)cyclohexane-1,4-dione [hereinafter referred to as "compound (IIIa)"] with malononitrile and then oxidizing the thus-obtained 2,5-bis(2-cyanoethyl) cyclohexane-1,4-bis(dicyanomethylene) [hereinafter referred to as "compound (IVa)"].

Production of compound (IIIa)

A mixture of 11.2 g (0.1 mole) of cyclohexane-1,4-dione, 21.3 g (0.3 mole) of pyrrolidine and 45 ml of toluene was refluxed for 3 hours in a nitrogen gas stream with byproduct water being removed.

The toluene and unreacted pyrrolidine were removed, 50 ml of dioxane and 15.9 g (0.3 mole) of acrylonitrile were added, and the mixture was refluxed for 12 hours. Thereafter, 5 ml of water was added and the refluxing was continued for another hour.

After completion of the reaction, the unreacted acrylonitrile and dioxane were removed from the reaction mixture, 300 ml of water was added, and the resultant mixture was extracted with chloroform.

The chloroform layer was washed with 10% hydrochloric acid and then with water, and dried over sodium sulfate. The chloroform was distilled off from the extract. The crystalline residue (10.9 g) was recrystallized from methanol to give a colorless crystalline product melting at 147.8° C.

This crystalline product was identified as the compound (IIIa), namely 2,5-bis(2-cyanoethyl)cyclohexane-1,4-dione, as a result of analysis of its NMR spectrum, mass spectrum and IR spectrum.

Production of compound (IVa)

A mixture of 873 mg of the compound (IIIa) obtained in the above manner, 3.4 g of water, 5.0 g of methanol and 9.9 mg of β-alanine was heated. When the reaction vessel inside temperature reached 45° C., a solution of 536 mg of malononitrile in 1.6 g of methanol was added all at once, and the reaction was conducted at 45–50° C. for 1.5 hours.

After completion of the reaction, the reaction mixture was cooled to room temperature, and the crystals were collected by filtration, washed with water and then with methanol, and dried under reduced pressure to give 1.24 g of a crystalline product.

This crystalline product had the characteristic values given below and was identified as the compound (IVa), namely, 2,5-bis(2-cyanoethyl)cyclohexane-1,4-bis(dicyanomethylene). The yield was 98.6 % based on the compound (IIIa).

| | |
|---|---|
| Melting point | 216–220° C. |
| IR (KBr), $\nu$ (cm$^{-1}$) | 3930, 2240, 1720, 1610, 1435 |
| NMR(DMSO — d$_6$), δ (ppm) | 1.6–3.5 (m, 14H) |
| Mass spectrum, M$^+$ | 314 |

Production of compound (Va)

A mixture of 0.94 g of the compound (IVa) obtained in the above manner and 31 g of acetonitrile was heated. When the inside temperature reached 70° C., a solution of 0.95 g of pyridine in acetonitrile and a solution of 0.98 g of bromine in acetonitrile were added at the same time, and the reaction was conducted at 70–75° C. for 15 minutes.

After completion of the reaction, the reaction mixture was cooled to room temperature, and the crystals were collected by filtration, washed with water, methanol and acetone in that order, and dried to give 0.58 g of a crystalline product.

The crystalline product obtained had the characteristic values given below and was identified as the compound (Va), namely 2,5-bis(2-cyanoethyl)-7,7,8,8-tetracyanoquinodimethane. The yield was 62.5% based on the compound (IVa).

| | |
|---|---|
| Melting point | 210–220° C. |
| IR (KBr), $\nu$ (cm$^{-1}$) | 2210, 1555, 1525, 1470, 1420, 890, 460 |

EXAMPLE 2

This example is concerned with 2,5-bis[2-(methoxycarbonyl)propyl]-7,7,8,8-tetracyanoquinodimethane as another example of the compound (V) of this invention. Said compound is hereinafter referred to as "compound (Vb)".

Said compound (Vb) is produced by reacting 2,5-bis[2-(methoxycarbonyl)propyl]cyclohexane-1,4-dione [hereinafter referred to as "compound (IIIb)"] with malononitrile and oxidizing the thus-obtained 2,5-bis[2-(methoxycarbonyl)propyl]cyclohexane-1,4-bis(dicyanomethylene) [hereinafter referred to as "compound (IVb)"].

Production of compound (IIIb)

A mixture of 11.2 g (0.1 mole) of cyclohexane-1,4-dione, dione, 21.3 g (0.3 mole) of pyrrolidine and 45 ml of benzene was refluxed in a nitrogen gas stream for 3 hours, with byproduct water being removed.

The benzene and unreacted pyrrolidine were removed, 50 ml of ethanol and 30.3 g (0.3 mole) of methyl methacrylate were added, and the resultant mixture was refluxed for 12 hours. Subsequently, 10 ml of water was added and hydrolysis was effected under reflux for 1 hour.

After completion of the reaction, the ethanol and unreacted methyl methacrylate were distilled off, 300 ml of water was added to the residue, and the mixture was extracted with chloroform. The extract was washed with 10% hydrochloric acid, the chloroform was then distilled off, and the residue was treated in a Kugelrohr vacuum distillation apparatus at an oven temperature of 190–210° C. (1.0–1.2 mmHg) to give a colorless viscous oil.

As a results of analysis of its NMR spectrum, mass spectrum and IR spectrum, the oil was identified as the compound (IIIb), namely 2,5-bis[2-(methoxycarbonyl)propyl]cyclohexane-1,4-dione.

Production of compound (IVb)

A mixture of 1.0 g of the compound (IIIb) obtained in the above manner, 3.5 g of water, 2.0 g of methanol and 8 mg of β-alanine was heated. When the inside temperature reached 45° C., a solution of 432 mg of malononitrile in 1.6 g of methanol was added all at once, and the reaction was carried out at 45–52° C. for 1.5 hours.

After completion of the reaction, the reaction mixture was cooled to room temperature, and the oil layer was separated and crystallized by addition of ether. The crystals were collected by filtration, washed with ether, and dried under reduced pressure to give 0.40 g of a crystalline product.

The crystalline product obtained had the characteristic values given below and was identified as the compound (IVb), namely 2,5-bis[2-(methoxycarbonyl)propyl]cyclohexane-1,4-bis(dicyanomethylene). The yield was 30.6 % based on the compound (IIIb).

| Melting point | 161–162° C. |
|---|---|
| IR (KBr), $\nu$ (cm$^{-1}$) | 2230, 1730, 1605, 1440, 1210, 1170 |
| NMR(DMSO — d$_6$), $\delta$ (ppm) | 3.59 (s, 6H), 3.5–1.5 (m, 12H), 1.12 (d, 6H) |
| Mass spectrum, M$^+$ | 408 |

Production of compound (Vb)

A mixture of 288.8 mg of the compound (IVb) obtained in the above manner and 10 g of acetonitrile was heated. When the inside temperature reached 70° C, a solution of 238 mg of pyridine in acetonitrile and a solution of 234 mg of bromine in acetonitrile were added simultaneously, and the reaction was conducted at 70–75° C. for 15 minutes.

After completion of the reaction, the reaction mixture was cooled to room temperature, and the acetonitrile was removed using an evaporator. Water was added, and the product crystals were collected by filtration, washed in sequence with water and methanol, and dried to give 169.5 mg of a crystalline product.

The crystalline product obtained had the characteristic values shown below and was identified as the compound (Vb), namely 2,5-bis[2-(methoxycarbonyl)propyl]7,7,8,8-tetracyanoquinodimethane. The yield was 59.3 % based on the compound (IVb).

| Melting point | 154–156° C. |
|---|---|
| IR (KBr), $\nu$ (cm$^{-1}$) | 2690, 2210, 1730, 1550, 1520, 1460, 1435, 1285, 1215, 1180, 1115, 985, 920 |
| NMR(CDCl$_3$), $\delta$ (ppm) | 7.30 (s, 2H), 3.68 (s, 6H), 3.5–2.6 (m, 6H), 1.35 (d, 6H) |

EXAMPLE 3

The procedure of Example 1 was followed except that methacylonitrile was used in lieu of acrylonitrile.

There was obtained 2,5-bis(2-cyanopropyl)cyclohexane1,4-dione [compound (IIIc)].

Said compound (IIIc) was reacted with malononitrile in the same manner as in Example 1 to give 2,5-bis(2-cyanopropyl)cyclohexane-1,4-bis(dicyanomethylene) [compound (IVc)].

This compound (IVc) was then oxidized in the same manner as in Example 1 except that N-bromosuccinimide was used in lieu of bromine. Formation of 2,5-bis(2-cyanopropyl)-7,7,8,8-tetracyanoquinodimethane could be confirmed.

Example 4

This example is concerned with 2,5-bis[2-(dimethylcarbamoyl)ethyl]-7,7,8,8-tetracyanoquinodimethane as a further example of the compound (V) of this invention. Said compound is hereinafter referred to as "compound (Vd)".

A mixture of 112.1 g (1.0 mole) of cyclohexane-1,4-dione, 213.4 g (3.0 moles) of pyrrolidine and 450 ml of toluene was refluxed in a nitrogen gas stream for 1.5 hours with byproduct water being removed. Thereafter, the toluene and unreacted pyrrolidine were removed. After cooling, 400 ml of dioxane and 297.4 g (3.0 moles) of N,N-dimethylacrylamide were added, and the reaction was conducted under reflux for 3 hours. Then, 100 ml of water was added, and the reaction was further conducted for 1 hour.

After completion of the reaction, the reaction mixture was cooled, the remaining N,N-dimethylacrylamide and dioxane were removed, 500 ml of water was added, and the mixture was extracted with chloroform. The chloroform layer was washed with 10% aqueous hydrochloric acid and then with water, and dried over sodium sulfate. Removal of the chloroform by distillation gave 72.4 g of crystals. Recrystallization from methanol-acetone gave white crystals.

These crystals had the characteristic values shown below and were identified as 2,5-bis[2-(dimethylcarbamoyl)ethyl]cyclohexane-1,4-dione (IIId).

| Melting point | 157–158° C. |
|---|---|
| IB (KBr), $\nu$ (cm$^{-1}$) | 3050–2800, 1705, 1640, 1500, 1420, 1395, 1340, 1265, 1145 |
| NMR (CDCl$_3$), $\delta$ (ppm) | 3.03 (s, 6H), 2.95 (s, 6H), 3.2–1.5 (m, 14H) |
| Mass spectrum, M$^+$ | 310 |

A mixture of 11.21 g (36.2 millimoles) of the compound (IIId) obtained in the above manner, 38.3 g of water, 22.3 g of methanol and 112 mg of β-alanine was heated to 40° C. A solution of 4.85 g (73.5 millimoles) of malononitrile in methanol was added dropwise and the reaction was allowed to proceed at 40–50° C. for 1.5 hours. After cooling, the resultant crystalline precipitate was collected by filtration, washed in sequence with water and methanol, and dried to give 8.92 g of a white crystalline powder.

The crystalline product thus obtained had the characteristic values given below and was identified as 2,5-bis[2-(dimethylcarbamoyl)ethyl]cyclohexane-1,4-bis(dicyanomethylene) (IVd).

| Melting point | 196–197° C. |
|---|---|
| IR (KBr), $\nu$ (cm$^{-1}$) | 2930, 2240, 1645, 1500, 1415, 1370, 1340, 1265, |

| | -continued |
|---|---|
| | 1125, 1060 |
| NMR (CDCl$_3$), δ (ppm) | 2.93 (s, 6H), 2.80 (s, 6H) |
| | 3.7–1.5 (m, 14H) |

A mixture of 4.06 g (10.0 millimoles) of the compound (IVd) obtained in the above manner and 60 g of acetonitrile was heated to 75° C., and 326 g (20.4 millimoles) of bromine was added dropwise and then 3.16 g (40.0 millimoles) of pyridine were added dropwise. After 15 minutes of heating at 75–80° C., the reaction mixture was cooled and the acetonitrile was distilled off under reduced pressure. Water and methanol were added to the residue, and the resultant crystals were collected by filtration, washed in sequence with water and methanol, and dried to give 2.43 g (6.0 millimoles) of brown crystals.

The crystalline product obtained had the characteristic values shown below and was identified as 2,5-bis[2-(dimethylcarbamoyl)ethyl]-7,7,8,8-tetracyanoquinodimethane (Vd).

| Melting point | 195–197° C. (decomposition) |
|---|---|
| IR (KBr), ν (cm$^{-1}$) | 2920, 2220, 1640, 1505, |
| | 1420, 1400, 1345, 1270, |
| | 1145, 1040, 920 |
| $^1$H-NMR (CDCl$_3$), δ (ppm) | 7.30 (s, 2H), 3.06 (s, 6H), |
| | 2.97 (s, 6H), 3.35 (t, 4H), |
| | 2.72 (t, 4H) |

| | -continued |
|---|---|
| $^{13}$C-NMR (CDCl$_3$), δ (ppm) | 169.4, 150.5, 142.8, 132.9, |
| | 113.5, 112.8, 87.0, 37.1, |
| | 35.6, 31.7, 27.9 |

What is claimed is:

1. A 2,5-disubstituted-7,7,8,8-tetracyanoquinodimethane of the general formula

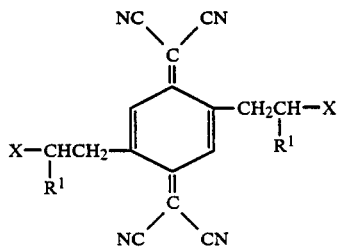

wherein R$_1$ is hydrogen or methyl, X is —CONR$^3$R$^4$, in which R$^3$ and R$^4$ each is hydrogen or C$_{1-4}$ alkyl, or —CN.

2. The compound of claim 1 which is 2,5-bis(2-cyanoethyl)-7,7,8,8-tetracyanoquinodimethane.

3. The compound of claim 1 which is 2,5-bis(2-cyanopropyl)-7,7,8,8-tetracyanoquinodimethane.

4. The compound of claim 1 which is a 2,5-bis2-(dialkylcarbamoyl)ethyl-7,7,8,8-tetracyanoquinodimethane.

* * * * *